United States Patent [19]

Budai et al.

[11] Patent Number: 4,588,435
[45] Date of Patent: May 13, 1986

[54] N-SUBSTITUTED AMINO PROPANE SULFONIC ACID DERIVATIVES AND PLANT GROWTH REGULATING USE

[75] Inventors: Zoltán Budai; Attila Kis-Tamás; Aranka Lay née Kónya; Zoltán Vig; Viktor Andriska; Tibor Mezei, all of Budapest, Hungary

[73] Assignee: EGYT Gyogyszervegyeszeti Gyar, Budapest, Hungary

[21] Appl. No.: 696,658

[22] Filed: Jan. 31, 1985

[30] Foreign Application Priority Data

Feb. 3, 1984 [HU] Hungary .................................. 448/84

[51] Int. Cl.⁴ ..................... A01N 37/22; A01N 43/08; C07C 143/63; C07D 307/68
[52] U.S. Cl. ........................................... 71/103; 71/88; 260/507 R; 549/487
[58] Field of Search .................... 549/487; 260/507 R; 71/88, 103

[56] References Cited

U.S. PATENT DOCUMENTS 4,046,911 9/1977 Hubele ................................ 549/487
4,442,117 4/1984 Kung et al. ................. 260/507 R X
4,494,983 1/1985 Eicken et al. ......................... 71/118

OTHER PUBLICATIONS

Butula et al, Chemical Abstracts, vol. 82 (1975), 111706x.

*Primary Examiner*—Richard L. Raymond
*Attorney, Agent, or Firm*—Keil & Weinkauf

[57] ABSTRACT

The invention relates to new N-substituted amino propane sulfonic acid derivatives of the Formula I

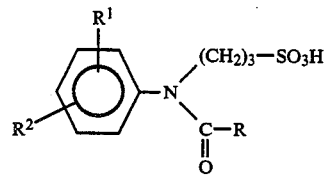

and salts and hydrates thereof, a process for the preparation thereof and plant growth regulating agents comprising the same wherein $R^1$ and $R^2$ may be identical or different and stand for hydrogen, halogen, lower alkyl or lower alkoxy and
R stands for furyl; or lower alkyl or phenyl the two latter groups being optionally substituted by one or more halogeno atom(s).

17 Claims, No Drawings

N-SUBSTITUTED AMINO PROPANE SULFONIC ACID DERIVATIVES AND PLANT GROWTH REGULATING USE

This invention relates to new N-substituted amino propane sulfonic acid derivatives, a process for the preparation thereof and compositions comprising the same.

The new compounds of the present invention possess useful plant growth regulating properties.

According to a feature of the present invention there are provided new compounds of the general Formula I

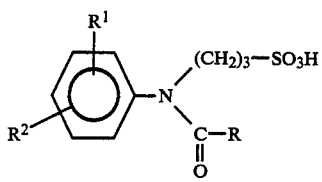

wherein
R$^1$ and R$^2$ may be identical or different and stand for hydrogen, halogen, lower alkyl or lower alkoxy and R stands for furyl; or lower alkyl or phenyl the two latter groups being optionally substituted by one or more halogeno atom(s) and hydrates and salts thereof.

The term "lower alkyl" as used throughout the specification relates to straight or branched chain alkyl groups having 1–4 carbon atoms (e.g. methyl, ethyl, n-propyl, isopropyl, n-butyl, etc.). Under the term "lower alkoxy" straight or branched chain alkyl ether groups comprising 1–4 carbon atoms are to be understood (e.g. methoxy, ethoxy). The term "halogen" encompasses the fluorine, chlorine, bromine and iodine atoms.

The R$^1$ and R$^2$ substituents are preferably attached to the 2-, 3-, 2,5-, 3,5- and 2,6-positions.

R as halogeno alkyl group may stand for e.g. for a chloro methyl, bromo methyl, iodo methyl, 2-chloro-ethyl group etc.

R as a halogeno phenyl group may be e.g. a 2-, 3- or 4-chloro-phenyl, 2-, 3- or 4-bromo-phenyl, 2,6-, 2,4- or 3,5-dichloro-phenyl group, etc.

In a preferred sub-group of the compounds of the general Formula I, R$^1$ and R$^2$ are lower alkyl and R is halogeno substituted lower alkyl.

Particularly preferred representatives of the compounds of the general Formula I are the following derivatives:

N-2',6'-dimethyl-phenyl-N-chloroacetyl-3-aminopropane-1-sulfonic acid;

N-2'-ethyl-phenyl-N-chloroacetyl-3-amino-propane-1-sulfonic acid and salts thereof.

The salts of the compounds of the general Formula I may be formed with inorganic or organic bases. Thus preferably alkaline or alkaline earth metal hydroxides or carbonates (e.g. sodium hydroxide, calcium carbonate, magnesium carbonate, potassium hydroxide etc.) or organic bases (e.g. triethyl amine) may be used for salt formation.

According to a further feature of the present invention there is provided a process for the preparation of compounds of the general Formula I and hydrates and salts thereof which comprises reacting a compound of the general Formula II

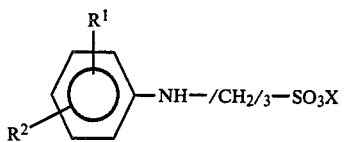

wherein R$^1$ and R$^2$ are as stated above and X stands for hydrogen or a leaving group with a carboxylic acid of the general Formula III

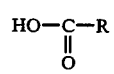

wherein R is as stated above or a reactive derivative thereof and, if a compound of the general Formula II is used wherein X is a leaving group, hydrolysing the product thus obtained and, if desired, converting a compound of the general Formula I thus obtained into a salt or setting free a compound of the general Formula I from a salt thereof.

X as a leaving group may preferably be a phenyl, benzyl or benzhydryl group.

The reactive derivative of the carboxylic acid of the general Formula III may preferably be an acid halide (e.g. acid chloride), amide, ester or anhydride. The free acid of the general Formula III may also be used; in this case the reaction is carried out in the presence of a dehydrating agent (e.g. dicyclohexyl carbodiimide).

The reaction of the compound of the general Formula II and the acid of the general Formula III or a reactive derivative thereof may be carried out by methods known per se. The reaction may be accomplished at a temperature between 20° C. and the boiling point of the reaction mixture, preferably under heating, particularly at the boiling point of the reaction mixture. If an amide of the acid of the general Formula III is used, it is preferred to work at a temperature of about 110°–120° C. If acylation is carried out by using an ester, the reaction temperature may be between 60° C. and 150° C. Acylation with acid anhydrides may be accomplished at a temperature not exceeding 70° C.

The reaction may be carried out in the absence or presence of an inert organic solvent. As organic solvent e.g. aromatic hydrocarbons (e.g. benzene or xylene), aliphatic hydrocarbons or ethers may be used.

The product thus obtained may be isolated from the reaction mixture by methods known per se (e.g. crystallization, filtration, evaporation etc.).

If compounds of the general Formula II are used wherein X stands for a leaving group (e.g. phenyl, benzyl or benzhydryl), the said leaving group is split off by subjecting the product obtained to hydrolysis.

The starting materials of the general Formula II are known compounds and can be prepared by known methods (e.g. C.A. 52, 10918a; C.A. 95, 150152b).

The carboxylic acid of the general Formula III and reactive derivatives thereof are known as well.

The N-substituted amino propane sulfonic acid derivatives of the general Formula I thus obtained may be converted into their salts by methods known per se by reacting the compound of the general Formula I with the corresponding base.

According to a still further feature of the present invention there are provided plant growth regulating agents comprising at least one compound of the general Formula I (wherein R, $R^1$ and $R^2$ are as stated above) or a hydrate or salt thereof as active ingredient in admixture with suitable inert solid or liquid carriers or diluents and optionally further additives.

The plant growth regulators of the present invention may contain 0.001–95% by weight of the compound of the general Formula I or a hydrate or salt thereof and the invention encompasses both the concentrates and ready-for-use compositions.

The compositions of the present invention may be formulated e.g. in the form of emulsifiable concentrates, granules, microgranules, foils (seed-dressing agents), wettable powders, sprays etc. or in any other suitable and conventional forms. The said compositions may comprise in addition to the active ingredient solid or liquid carriers, diluents, solvents, additives, auxiliary agents etc.

The auxiliary agents may be surfactants (e.g. wetting, emulsifying and dispersing agents, disintegrating agents, lubricants, colourants, adhesives, anticorrosive agents and additives improving adhesion or absorption etc.).

The solid carriers or diluents may be inert mineral materials (e.g. aluminium silicate, talc, calcinated magnesium oxide, diatomaceous earth, tricalcium phosphate, cork-wood powder, powdered coke, clay, kaoline, perlite, bentonite, montmorrilonite, attapulgite clay, pyrophilite, dolomite, gypsum, calcium phosphate, calcium carbonate, mica slate, colloidal silicium dioxide, Fuller's earth, Hewitt's earth, porcelain earth etc.).

The suitable liquid carriers and diluents may be aqueous, organic or aqueous organic solvents, e.g. water, ketones (e.g. acetophenone, cyclohexanone, isophorone), aromatic hydrocarbons (e.g. benzene, toluene, xylene, alkyl naphthalenes, tetrahydro-naphthalene), chlorinated hydrocarbons (e.g. chloro benzenes, ethylene dichloride, trichloro ethylene, tetrachloro ethane), alcohols (e.g. methanol, ethanol, isopropanol, butanol, propyleneglycole, diacetone alcohol etc.), kerosin, animal, vegetable and mineral oils (aliphatic mineral oil fractions, mineral oil fractions having a high aromatic content, e.g. kerozine), polar organic solvents (e.g. dimethyl sulfoxide, dimethyl formamide) and mixtures thereof.

The wetting, dispersing and emulsifying agents may be of the ionic or non-ionic type.

The non-ionic surfactant may be e.g. a condensation product of ethylene oxide formed with $C_{10-20}$ fatty alcohols (e.g. oleyl alcohol, cetyl alcohol, octadecyl alcohol etc.), alkyl phenols (e.g. octyl phenol, nonyl phenol, octyl cresole), amines (e.g. oleyl amine etc.), mercaptanes (e.g. dodecyl mercaptane, etc.) or carboxylic acids; partial esters of long-chained fatty acids and hexitol anhydrides; condensation products of the said partial esters and ethylene oxide; lecitines and fatty acid esters of polyalcohols.

As suitable cationic surfactants quaternary ammonium compounds (e.g. cetyl trimethyl ammonium bromide etc.) may be used.

The suitable anionic surfactants may be soaps; salts of aliphatic monoesters of sulfuric acid (e.g. sodium lauryl sulfate, sodium salts of the sulfate of dodecyl alcohol); salts of sulfonated aromatic compounds (e.g. sodium lauryl dodecyl benzene sulfonate, sodium, calcium or ammonium lignosulfonate, butyl naphthalene sulfonate and a mixture of the sodium salts of diisopropyl and triisopropyl naphthale sulfonic acid); sodium salt of a petroleum sulfonic acid; the potassium or triethanol amine salt of oleic acid and abietic acid.

As suitable suspending agents e.g. hydrophilic colloides (e.g. polyvinyl pyrrolidone, sodium carboxy methyl cellulose) and vegetable gums (e.g. tragacant gum) may be applied.

Suitable adhesion improving agents are the calcium or magnesium stearate, adhesive substances (e.g. polyvinylalcohol) or cellulose derivatives.

As dispersing agent e.g. methyl cellulose, lignine sulfonates and alkyl naphthalene sulfonates may be used.

As agents improving distribution, adhesion, rain resistance and penetration e.g. fatty acids, resins, caseine and alginates may be used.

The active ingredient may be admixed with the above carriers, diluents, and auxiliary agents to yield various solid or liquid compositions suitable for use in agriculture and horticulture.

The solid compositions may be e.g. dusting powders, granules, preferably microgranules, coated seed-grains (wherein the coating is applied onto the surface of the seed in the form of a thin film or a thicker layer) and seed-foils for use in horticulture.

The liquid compositions may be solutions, sprayable aqueous solutions, solutions formed with organic solvents including oily solutions and miscible oils-dispersions, suspensions (preferably aqueous suspensions) aqueous or oily emulsions, inverse emulsions.

The granulated compositions may be prepared by dissolving a compound of the general Formula I in a solvent, applying the solution in the presence of a suitable binder onto the surface of a granular substance (e.g. pumice or attaclay; mineral non-porous granules, e.g. sand or clay-earth; organic granules e.g., black earth or cut tobacco stems etc.) and optionally drying. The granular compositions may also be prepared by pressing the active ingredient with powdered mineral substances in the presence of a lubricant and a binder, grinding the pressed material and, if desired, sieving the same to the desired particle size. Granular compositions may be prepared preferably by means of dry or moist granulating.

According to a preferred embodiment of the invention there are provided seed-grain foils. It is known that in horticulture and other agricultural procedures in order to facilitate the sowing of seeds and to ensure uniform seed- and row-distances manual sowing (planting) is often replaced by incorporating the seeds into a water-soluble foil and placing the said foil-strips (which may optionally contain the seeds in several rows) into the soil. The foil may be prepared of any water-soluble material being inert towards the seed (e.g. polyvinyl alcohol). The only requirements raised against the foil materials are that it should not damage the seeds and should disintegrate in the soil under the effect of moisture or dissolve in it. The seed-foil according to the present invention may comprise the active ingredient being incorporated in the foil or the seeds treated with the active ingredient may be placed into the foil. The particular advantage of seed-grain foils resides in the fact that the germinating ability of the seeds is increased, the growth of cultivated plants is enhanced and an effective protection is provided against insect pests in the initial growth period of the plants.

Dispersions, suspensions and emulsions are prepared by dissolving the active ingredient of the general Formula I in a solvent which may optionally comprise one or more wetting, dispersing, suspending or emulsifying agent(s), adding the mixture thus obtained to water which in turn may optionally also comprise one or more wetting, dispersing or emulsifying agent(s).

Emulsifiable oils may be prepared by dissolving or finely dispersing the active ingredient of the general Formula I in a suitable slightly water-miscible solvent in the presence of an emulsifier.

Sprays suitable for direct use may be prepared by dissolving an active ingredient of the general Formula I in a solvent having a high or medium boiling point, the said solvent boiling preferably at a temperature above 100° C.

An inverse emulsion may be prepared by emulsifying an emulsion of a compound of the general Formula I before or during spraying in water in a spraying device.

Aqueous compositions may be preferably prepared from emulsion concentrates, pastes and wettable powders having a high active ingredient content which may be diluted before use to the desired concentration with water.

The said concentrates can be stored for a longer period of time and form after storage on diluting with water aqueous compositions which are sufficiently homogeneous to enable the use of a conventional spraying apparatus. The active ingredient content of the concentrates amounts generally to 10–85% by weight and is preferably 25–60% by weight. The active ingredient content of the ready-for-use sprays amounts generally to 0.001–3.0% by weight, but may be higher or lower than the said interval as well, depending on the conditions of the given field of application.

The active ingredient content of the plant growth regulating agents of the present invention may vary between wide ranges and depends on several factors (e.g. the method of preparation, the field and mode of application etc.) and is in the range between 0.001 and 95% by weight. When used according to the "ultra low volume" method it is expedient to apply a composition having a very high active ingredient content of 90–95% by weight and comprising only a very small amount of additives. The said compositions can be applied to the plants or the soil in the form of a very fine dust preferably from an aeroplane. The active ingredient content of diluted compositions may be 0.01–20% by weight and that of more concentrated agents 20–95% by weight.

The active ingredient content of the emulsifiable concentrates amounts to 5–70% by weight—preferably 10–50% by weight—and that of powder mixtures is 0.4–10% weight—preferably 1–5% by weight.

The compositions of the present invention may be prepared by any suitable method known per se.

The compositions of the present invention may be used in the form of a spray, dusting powder, seed-dressing agent, seed-foil, soil watering liquid, dipping bath etc. The specific formulation depends on the particular field of application and is selected by taking into consideration all factors involved.

Seed-dressing may be carried out by coating the seeds with a mixture of the active ingredient of the general Formula I and carriers under stirring. One may also proceed by applying the active ingredient, an above surfactant and optionally a carrier onto the surface of the seeds. In the latter case the mixture of the active ingredient, surfactant and carrier is first wetted with a small amount of water and the seeds are then admixed with the suspension.

Seed-dressing may also be carried out by means of dragée-formation by placing the seeds into a dragée-pan and wetting the seed in the rotating pan with an aqueous solution of a binder (e.g. carboxy methyl cellulose sodium). The powder mixture of the coating components is then sprayed onto the surface of the wet seeds. The coating mixture is added until the desired coating thickness is reached.

One may also proceed by admixing the active ingredient with sand, soil or an above powdered solid carrier and optionally with one or more of the above surfactants and applying the powder mixture thus obtained into the drills when the seeds are sown.

The active ingredient may be applied onto the seeds in the form of an aqueous spray comprising one or more of the above surfactants and/or powdered carriers before, during or after sowing.

One may also proceed by applying the plant growth regulating agent of the present invention to the environment of the plant, onto the plant or onto certain parts of the plant (e.g. leaves) by spraying, dusting or by any other suitable method or by applying the same onto the soil (e.g. by means of watering solution, irrigation) or incorporating the composition into the soil whereby the seeds are sown into the drills of the soil treated with the composition.

The plant growth regulating compositions may be used both on mono- and dicotylodenous plants. The compositions of the present invention are suitable for pre-sowing, pre-planting, pre-emergent or post-emergent treatment or can be incorporated into the soil.

According to pre-sowing and pre-planting treatment the composition is applied onto the soil before the sowing of the seeds, while sowing or planting are carried out after the treatment of the soil.

According to pre-emergent treatment the compositions of the present invention are applied onto the soil before the emergence of the plant e.g. the soil is sprayed with the composition at a stage when the seeds have not yet broken the surface of soil.

According to post-emergent treatment the composition of the present invention are applied onto the area to be treated (e.g. parts of the plant or the soil) after the emergence of the plant.

It has been found that the compositions of the present invention are particularly efficient plant growth regulators in maize, sunflower, lettuce, cucumber, tomato, French beans and mustard cultures. In addition to enhancing the growth of plants in the vegetative period, the compositions of the present invention increase crop yield in the generative phase too.

The effective dose of the compounds of the general Formula I depends on several factors, e.g. the type and stage of the cultivated plant to be treated, the growth stage of the plant (e.g. seed, seedling, one-three leave stage etc.), the other plants growing in the environment of the plant to be treated, the season, climatic conditions and the method of treatment used (pre-sowing, pre-planting, pre-emergent, post-emergent etc.). The most effective dose is to be determined in each case by means of experiments. As a general guideline it can be stated that the dose may be in the range of 0.1–25 kg of active ingredient/ha preferably 0.1–15 kg of active ingredient/ha. For the enhancement of germination and seed-dressing a dose of 5–500 g/100 kg of seeds and for plant growth promotion, crop yield increase and soil treatment a dose of 0.1-15 kg/ha may be preferably used.

The compositions of the present invention may be used in various dilutions depending on the field of application (e.g. seed-dressing, treatment of foliage or soil etc.). Thus for seed-dressing, the improvement of germination ability and foliage treatment diluted compositions having an active ingredient content of 0.5-10,000 ppm—preferably 1-1000 ppm—may be used. For pre-emergent or post-emergent spraying diluted compositions (sprays) having an active ingredient content of 0.1-3.0% by weight—preferably 0.3-1% by weight—may be used.

The plant growth promoting activity of the compounds of the general Formula I may be illustrated by the following tests:

I. GLASS-HOUSE TESTS

1. Treatment of forced lettuce in a foil tent provided with a water-screen

In a foil-tent provided with a water-screen lettuce (Lucia) forced on a 2 m² plot is treated with a spray prepared according to Example 9 comprising as active ingredient the compound of Example 1 and 3, respectively (500 l/ha). Watering is carried out once during the growth period and five treatments are accomplished. The first treatment is carried out two weeks after planting and the further treatments are effected every second week. Four replicates are carried out and the results are expressed as an average of the experiments. The results are summarized in Table I where the average weight of the heads of lettuce is given for each plot at various doses (kg/lettuce).

TABLE I

| Test compound Example No. | Dose kg/ha | | | Untreated control |
|---|---|---|---|---|
| | 1 | 3 | 5 | |
| 1 | 0.1775 | 0.2075ˣ | 0.2125ˣ | 0.1750 |
| 3 | 0.1600 | 0.1800 | 0.1975ˣ | 0.1650 |

ˣThe results differ significantly (>5%) from the control.

In Table II the effect of a composition according to Example 9 comprising an active ingredient the product of Example 1 on the crop yield per plot is disclosed.

TABLE II

| Dose | Crop yield per plot/kg/plot/ |
|---|---|
| 1 | 8.875 |
| 3 | 10.375ˣ |
| 5 | 10.628ˣ |
| Untreated control | 8.250 |

ˣThese results differ significantly from the control.

2. Treatment of cucumber in a heated foil-tent under forced conditions

The plants are planted in a foil-tent at a four weeks' seedling stage. Row-distance: 50 cm; stem-distance: 20 cm; the soil is loose and humous. Watering is continuous (10 l/m²). As nutrient medium 3 kg of cattle-dung/m² is used. Five plants are trained on a support at each m². Treatment is carried out by using three different doses of a spray prepared according to Example 9 and comprising as active ingredient a compound of Example 1 and 3, respectively. Number of replicates: 4.

The crop yields obtained are summarized in Table III.

TABLE III

| Test compound Example No. | Dose kg/ha | Crop yield /dkg/ | Crop yield /as % of the control/ |
|---|---|---|---|
| 1 | 1 | 357 | 128 |
| | 3 | 449 | 160 |
| | 5 | 485 | 173 |
| 3 | 1 | 301.8 | 107 |
| | 3 | 376.6 | 135 |
| | 5 | 436.5 | 155 |
| Untreated control | | 280 | 100 |

3. Determination of the germination of mustard 500 seeds are sown in a dissemination box. The soil was treated before sowing with various doses of a composition according to Example 9 comprising as active ingredient a compound of Examples 1 and 3, respectively. Watering is carried out after sowing. The average temperature amounts to 19.5° C.

Germination is observed the 5th and 9th day after sowing. The results are disclosed in Table IV.

TABLE IV

| Test compound Example No. | Dose kg/ha | Germination, % | |
|---|---|---|---|
| | | 5th day | 9th day |
| 1 | 1 | 72 | 90 |
| | 3 | 81 | 86 |
| | 5 | 91 | 91 |
| 3 | 1 | 77 | 89 |
| | 3 | 80 | 85 |
| | 5 | 91 | 91 |
| Control | — | 79 | 80 |

4. Determination of the green weight and dry weight of maize

Five grains of maize (type: Coll. 440) pro pot are sown in river sand. The composition according to Example 9 comprising as active ingredient a compound according to Examples 1, 2 and 3, respectively was incorporated into the soil before sowing. The average temperature amounts to 21° C. The number of replicates is 4. The results are summarized in Table V.

TABLE V

| Test compound Example No. | Dose kg/ha | Green weight | | Dry weight | |
|---|---|---|---|---|---|
| | | g | % of control/ | g | % of control |
| 1 | 1 | 69 | 172 | 9 | 180 |
| | 2 | 89 | 222 | 9 | 180 |
| | 5 | 56 | 140 | 5 | 100 |
| 2 | 1 | 86 | 215 | 10 | 200 |
| | 2 | 71 | 177 | 8 | 160 |
| | 5 | 43 | 107 | 6 | 120 |
| 3 | 1 | 97 | 242 | 10 | 200 |
| | 2 | 90 | 225 | 10 | 200 |
| | 5 | 67 | 167 | 7 | 140 |
| Untreated control | — | 40 | 100 | 5 | 100 |

5. Measurement of the height of sunflower

The experimental conditions are the same as disclosed in the preceding paragraph. Strain: GK-70. The average temperature amounts to 22° C. The height is measured on the 8th day after sowing. The results are set forth in Table VI.

TABLE VI

| Test compound Example No. | Dose kg/ha | Height | |
|---|---|---|---|
| | | cm | % of control |
| 1 | 1 | 8 | 228 |
| | 2 | 10.5 | 300 |

TABLE VI-continued

| Test compound Example No. | Dose kg/ha | Height cm | % of control |
|---|---|---|---|
| | 5 | 8 | 228 |
| 2 | 1 | 6 | 171 |
| | 2 | 7 | 200 |
| | 5 | 3.5 | 100 |
| | | 3.5 | 100 |
| 3 | 1 | 7 | 200 |
| | 2 | 8 | 228 |
| | 5 | 8 | 228 |
| Untreated control | | 3.5 | 100 |

6. Measurement of the height of Hungarian millet (*Setaria italica*)

20 g of Hungarian millet grains are sown into a vessel having a diameter of 170 mm. As soil washed river sand is used. The average temperature amounts to 22° C. Pre-emergent treatment is carried out by using a composition according to Example 9 comprising an active ingredient the compound of Example 1. The dose is 1 kg/ha. On the 20th day the height of the plants is by 33% higher than that of the untreated control.

II. FREELAND EXPERIMENTS

Test plants:
  maize MUTC 596
  sunflower GK-70
  tomato K-3 $F_1$
  cucumber "budai félhosszu"
  French beans CHEROKEE Type of soil: semibound soil.
Treatment: Van der Wei sprayer with logarithmical dose change
Plot size: 2×20 m, 40 m².

1. Measurement of the height of maize

Treatment is carried out by using a composition according to Example 9 comprising as active ingredient a compound of Examples 1 and 3, respectively. Results are registered five weeks after pre-emergent treatment and 20 days after post-emergent treatment. The result are summarized in Table VII.

TABLE VII

| Test compound Example No. | Method of treatment | Dose kg/ha | Height of plants % of untreated control |
|---|---|---|---|
| 1 | pre-emergent | 3.6 | 142.3 |
| | | 2.8 | 135.0 |
| | | 2.25 | 129.1 |
| | | 1.8 | 130.5 |
| | post-emergent | 2.8 | 120.9 |
| | | 2.25 | 112.7 |
| | | 1.8 | 116.9 |
| 3 | pre-emergent | 3.6 | 130.7 |
| | | 2.8 | 134.5 |
| | | 2.25 | 141.8 |
| | | 1.8 | 102.1 |
| | post-emergent | 7.2 | 121.6 |
| | | 5.7 | 119.7 |

2. Measurement of the height of sunflower

The composition according to Example 9 comprising as active ingredient a compound according to Examples 1 and 3, respectively is used. The height of the plants is measured 5 days after pre-emergent treatment. The results are shown in Table VIII.

TABLE VIII

| Test compound Example No. | Dose kg/ha | Height of plant in % of the untreated control |
|---|---|---|
| 1 | 3.6 | 145.6 |

TABLE VIII-continued

| Test compound Example No. | Dose kg/ha | Height of plant in % of the untreated control |
|---|---|---|
| | 2.8 | 170.5 |
| | 2.25 | 158.9 |
| | 1.8 | 138.7 |
| 3 | 5.7 | 140.8 |
| | 4.5 | 136.5 |
| | 2.8 | 139.7 |

3. Effect on the crop weight of tomato

Treatment is carried out by using a composition according to Example 9 comprising as active ingredient a compound according to Example 1, 2 and 3, respectively. The crop weight is determined at the end of the growth period. The results are set forth in Table IX.

TABLE IX

| Test compound Example No. | Method of treatment | Dose kg/ha | Crop yield % of control |
|---|---|---|---|
| 1 | pre-emergent | 5.7 | 134.0 |
| | | 4.5 | 124.6 |
| | | 2.8 | 123.3 |
| | | 2.25 | 115.3 |
| | post-emergent | 5.7 | 108.0 |
| | | 4.5 | 120.0 |
| 2 | pre-emergent | 5.7 | 118.8 |
| | | 4.5 | 107.3 |
| | | 3.6 | 110.0 |
| | post-emergent | 2.25 | 109.1 |
| | | 1.8 | 106.8 |
| 3 | pre-emergent | 5.7 | 123.3 |
| | | 4.5 | 133.3 |
| | | 3.6 | 116.6 |
| | post-emergent | 5.7 | 106.6 |
| | | 4.5 | 196.6 |

4. Effect on the crop weight of French beans

The treatment is carried out by using the composition according to Example 9 comprising as active ingredient a compound of Example 1 and 3, respectively. Crop weight is determined at the end of the growth period. The results are summarized in Table X.

TABLE X

| Test compound Example No. | Method of treatment | Dose kg/ha | Crop yield % of control |
|---|---|---|---|
| 1 | pre-emergent | 3.6 | 126.3 |
| | | 2.8 | 121.0 |
| | | 2.25 | 121.0 |
| | | 1.8 | 115.0 |
| | post-emergent | 3.6 | 116.3 |
| | | 2.8 | 117.3 |
| | | 2.25 | 121.0 |
| | | 1.8 | 117.3 |
| 3 | pre-emergent | 4.5 | 132.6 |
| | | 3.6 | 123.1 |
| | | 2.8 | 137.3 |
| | post-emergent | 3.6 | 115.7 |
| | | 2.8 | 110.5 |

5. Effect on the ear of maize

Treatment is carried out by using a composition according to Example 9 comprising as active ingredient a compound of Example 1 and 3, respectively. The weight of the ear of maize is weighed at the end of the growth period. The results are summarized in Table XI.

TABLE XI

| Test compound Example No. | Method of treatment | Dose kg/ha | Weight of ear of maize in % of control |
|---|---|---|---|
| 1 | pre-emergent | 4.5 | 128.5 |

TABLE XI-continued

| Test compound Example No. | Method of treatment | Dose kg/ha | Weight of ear of maize in % of control |
|---|---|---|---|
|   |   | 3.6 | 114.2 |
|   |   | 2.8 | 112.8 |
|   | post-emergent | 4.5 | 137.1 |
|   |   | 3.6 | 142.8 |
|   |   | 2.8 | 115.0 |
| 3 | pre-emergent | 4.5 | 128.5 |
|   |   | 3.6 | 114.2 |
|   |   | 2.8 | 127.1 |
|   |   | 2.25 | 128.5 |

6. Effect of the crop weight of sunflower

Pre-emergent treatment is carried out by using the composition according to Example 9 comprising the compound of Examples 1, 2 and 3, respectively. The results are summarized in Table XII.

TABLE XII

| Test compound Example No. | Dose kg/ha | Crop yield in % of control |
|---|---|---|
| 1 | 1.4 | 112.9 |
|   | 1.1 | 112.9 |
| 2 | 2.8 | 121.4 |
|   | 2.25 | 112.8 |
|   | 1.8 | 111.4 |
| 3 | 1.1 | 161.2 |

Further details of the present invention are to be found in the following Examples without limiting the scope of protection to the said Examples.

EXAMPLE 1

N-2',6'-dimethyl-phenyl-N-chloroacetyl-3-amino-propane-1-sulfonic acid

A mixture of 24.3 g (0.1 mole) of N-/2',6'-dimethyl-phenyl-3-amino-propane-1-sulfonic acid and 60 ml of chloro acetyl chloride is heated to boiling for an hour. The excess of chloro acetyl chloride is distilled off in vacuo. The residue is dissolved in 60 ml of ethyl acetate, clarified with activated charcoal, whereupon 3.6 g (0.2 mole) of water are added and the solution is allowed to crystallize overnight. Thus 29.35 of the desired compound are obtained in the form of colourless crystals. Yield 82.5%. The dihydrate melts at 146°–148° C.

Analysis: for the Formula $C_{13}H_{18}ClNO_4S \cdot 2H_2O$ (355.833). Calculated: C: 43.88%, H: 6.23%, Cl: 9.96%, N: 3.93%, S: 9.01%. Found: C: 43.86%, H: 6.20%, Cl: 9.95%, N: 396%, S: 9.95%.

The calcium salt-i.e. calcium-bis-[2',6'-dimethyl-phenyl-N-chloroacetyl-3-amino-propyl-sulfate]-melts at 195°–200° C. decomposition.

Analysis: for the Formula $C_{13}H_{17}ClNO_4S_2Ca$ (677.670). Calculated: C: 46.08%, H: 5.05%, Cl: 10.46%, N: 4.12%, S: 9.46%. Found: C: 46.12%, H: 5.10%, Cl: 11.37%, N: 4.05%, S: 9.50%.

EXAMPLE 2

N-3',5'-dimethyl-phenyl-N-chloro-acetyl-3-amino-propane-1-sulfonic acid 24.3 g (0.1 mole) of N-3',5'-dimethyl-phenyl-3-amino-propane-1-sulfonic acid and 60 ml of chloro acetyl chloride are reacted in an analogous manner to Example 1. Thus 27.14 g of the desired compound are obtained, yield 76.3%. The dihydrate melts at 72°–73° C.

Analysis: for the Formula $C_{13}H_{18}ClNO_4S \cdot 2H_2O$ (355.833). Calculated: C: 43.88%, H: 6.23%, Cl: 9.96%, N: 3.93%, S: 9.01%. Found: C: 43.90%, H: 6.25%, Cl: 9.82%, N: 3.92%, S: 9.14%.

The calcium-bis-[3',5'-dimethyl-phenyl-N-chloroacetyl-3-amino-propyl-sulfate] melts at 330° C.

Analysis: for the Formula $C_{13}H_{17}ClNO_4S_2Ca$ (677.670). Calculated: C: 46.08%, H: 5.05%, Cl: 10.46%, N: 4.12%, S: 9.46%. Found: C: 45.98%, H: 5.07%, Cl: 10.42%, N: 4.05%, S: 9.50%.

The magnesium-bis-[N-3',5'-dimethyl-phenyl-N-chloroacetyl 3-amino-propyl-sulfate] melts at 96°–98° C.

Analysis for the Formula $C_{13}H_{17}ClNO_4S_2Mg \cdot 4H_2O$ (733.974). Calculated: C: 42.54%, H: 5.76%, Cl: 9.66%, N: 3.81%, S: 8.73%. Found: C: 42.38%, H: 5.80%, Cl: 9.38%, N: 3.78%, S: 8.68%.

EXAMPLE 3

N-2'-ethyl-phenyl-N-chloroacetyl-3-amino-propane-1-sulfonic acid

One proceeds according to Example 1 except that 24.3 g (0.1 mole) of N-2'-ethyl-phenyl-3-amino-propane-1-sulfonic acid and 60 ml of chloro acetyl chloride are used as starting material and to the ethyl acetate solution of the product 1.8 g (0.1 mole) of water are added. Thus 24.6 g of the desired compound are obtained in the form of colourless crystals, yield 78.4%. The monohydrate melts at 87°–90° C.

Analysis: for the Formula $C_{13}H_{18}ClNO_4S$ (337.817). Calculated: C: 46.22%, H: 5.96%, Cl: 10.49%, N: 4.14%, S: 9.49%. Found: C: 46.29%, H: 5.96%, Cl: 10.46%, N: 4.09%, S: 9.55%.

EXAMPLE 4

N-2'-ethyl-6'-methyl-phenyl-N-chloroacetyl-3-amino-propane-/1/-sulfonic acid

One proceeds according to Example 1 except that 25.7 g (0.1 mole) of N-2'-ethyl-6'-methyl-phenyl-3-amino-propane-(1)-sulfonic acid and 75 ml of chloro acetyl chloride are used as starting material. Thus, 27.87 g of the desired compound are obtained, yield 83.5%. The colourless crystals melt at 155°–157° C.

Analysis: for the Formula $C_{14}H_{20}ClNO_4S$ (333.831). Calculated: C: 50.36%, H: 6.03%, Cl: 10.62%, N: 4.19%, S: 9.60%. Found: C: 50.25%, H: 6.02%, Cl: 10.66%, N: 4.16%, S: 9.54%.

EXAMPLE 5

N-2'-ethyl-6'-methyl-phenyl-N-dichloroacetyl-3-amino-1-propane-sulfonic acid

A mixture of 25.7 g (0.1 mole) of N-2'-ethyl-6'-methyl-phenyl-3-amino-1-propane-sulfonic acid and 75 ml of dichloro acetyl chloride is heated to boiling for 2 hours. The excess of dichloro acetyl chloride is distilled off in vacuo. Thus 32.22 g of the desired compound are obtained in the form of a colourless oil, yield 87.5%; $n_D^{25} = 1.531$.

Analysis: for the Formula $C_{14}H_{19}Cl_2SNO_4$ (368.274). Calculated: C: 45.65%, H: 5.20%, Cl: 19.25%, N: 3.80%, S: 8.70%. Found: C: 45.57%, H: 5.18%, Cl: 19.15%, N: 3.82%, S: 8.90%.

The triethylamino-[N-2'-ethyl-6'-methyl-phenyl-N-dichloroacetyl-3-amino-propyl-sulfate] melts at 130° C.

Analysis: for the Formula $C_{20}H_{34}Cl_2N_2O_4S$ (469.466). Calculated: C: 51.16%, H: 7.29%, Cl: 15.10%, N: 5.96%, S: 6.82%. Found: C: 51.20%, H: 7.32%, Cl: 15.12%, N: 5.92%, S: 6.79%.

EXAMPLE 6

N-2',6'-dimethyl-phenyl-N-dichloroacetyl-3-amino-propane-1-sulfonic acid

One proceeds according to Example 5 except that 24.3 g (0.1 mole) of N-2',6'-dimethyl-phenyl-3-amino-propane-1-sulfonic acid and 75 ml of dichloro acetyl chloride are used. Thus 28.16 g of the desired compound are obtained, yield 79.5%, $n_D^{25}=1.514$.

Analysis: for the Formula $C_{13}H_{17}Cl_2NO_4S/354.254/$. Calculated: C: 44.07%, H: 3.99%, Cl: 20.01%, N: 3.95%, S: 9.05%. Found: C: 44.12%, H: 3.91%, Cl: 20.15%, N: 3.90%, S: 9.10%.

EXAMPLE 7

N-2'-ethyl-6'-methyl-phenyl-N-3'',5''-dichloro-benzoyl-3-amino-propane-1-sulfonic acid To a suspension of 25.7 g (0.1 mole) of N-2'-ethyl-6'-methyl-phenyl-3-amino-propane-1-sulfonic acid and 200 ml of anhydrous benzene 20.2 g (0.2 mole) of triethyl amine are added at 0° C. After stirring for half an hour a solution of 21 g (0.1 mole) of 3,5-dichloro-benzoyl chloride and 20 ml of anhydrous benzene is added dropwise. The reaction mixture is stirred at room temperature for half an hour whereupon the benzene solutions are acidified with alcohol containing hydrochloric acid and the precipitated triethyl amine hydrochloride is filtered off. The benzene solution is washed with water, dried and evaporated. The residue is recrystallized from ethyl acetate. Thus 28.45 g of the desired compound are obtained, yield 65.4%. The colourless crystals melt at 210°–215° C.

Analysis: for the Formula $C_{19}H_{25}Cl_2NO_4S$ (434.374). Calculated: C: 52.53%, H: 5.80%, Cl: 16.33%, N: 3.23%, S: 7.38%. Found: C: 52.70%, H: 5.75%; Cl: 16.17%, N: 3.32%, S: 7.30%.

EXAMPLE 8

N-2'-ethyl-6'-methyl-phenyl-N-[furane-2-carbonyl]-3-amino-propane-1-sulfonic acid One proceeds according to Example 7 except that 25.7 g 0.1 mole of N-2'-ethyl-6'-methyl-phenyl-3-amino-propane-1-sulfonic acid, 20.2 g (0.2 mole) of triethyl amine and 13.05 g (0.1 mole) of furane-2-carbonyl chloride are used. Thus, 22.0 g of the desired compound are obtained, yield 62.6%. The colourless crystals melt at 84°–86° C.

Analysis: for the Formula $C_{17}H_{21}NO_5S$ (351.414). Calculated: C: 58.10%, H: 6.02%, N: 3.98%, S: 9.12%. Found: C. 58.15%, H: 6.10%, N: 4.00%, S: 9.20%.

EXAMPLE 9

Wettable powder (77 WP)

85% by weight of N-2'-ethyl-phenyl/-N-chloroacetyl-3-amino-propane-1-sulfonic acid dihydrate and 15% by weight of active silicic acid (Aerosil 250, Degussa AG) are homogenized. The homogenous powder mixture is ground in a mill whereupon 10% by weight of Arkopon T (Hoechst AG) wetting agent are added. The mixture is homogenized again. The wettable powder thus obtained comprises 77% by weight of the active ingredient and can be diluted with water to yield a spray of optional concentration.

The above process can be carried out by using the compounds prepared according to Examples 1, 2, 4, 5a, 7 and 8 as well.

EXAMPLE 10

Emulsifiable concentrate

50% by weight of the compound according to Example 5 are dissolved in 45% by weight of xylene. To the solution 2% by weight of Atlox 3368B emulsifier and 3% by weight of Atlox 4851B emulsifier (Atlas Co. Belgium) are added. The emulsifiable concentrate thus obtained comprises 50% by weight of the active ingredient and can be diluted with water to yield an emulsion of optional concentration.

The above process can also be carried out by using as active ingredient the compound prepared according to Example 6.

Seed dressing agents are prepared as follows:

500 g of the above composition are added to 3 l of a 2% aqueous Bermocoll E (Berol Kemi AG Sweden) solution under vigorous stirring. The emulsion thus obtained is sprayed onto 100 kg of maize seed-grains in a dragée-pan and the system is stirred for 30 minutes. At the end of this operation a uniform film is formed on the surface of the seed-grains comprising 250 g of the active ingredient pro 100 kg of seed-grains.

EXAMPLE 11

Powder mixture having an active ingredient content of 5%

5% by weight of the compound according to Example 5 are kneaded with 10% by weight of Aerosil 250 in a Z-armed kneader. Kneading is continued until the mixture disintegrates to a powder (about 10–30 minutes are required depending on the type of the kneader). To the powder mixture thus obtained 1 part by weight of Arkopon T powder are added and stirring is continued until a completely uniform mixture is formed. The homogenized mixture is then homogenized with 84% by weight of precipitated chalk powder in a kneader. The powder mixture is finely ground in a mill. Thus a wettable powder having an active ingredient content of 5% by weight is obtained which can be converted by diluting with water into a stable spray suitable for the treatment of plants.

The above process can also be carried out by using the compound according to Example 6 as active ingredient.

EXAMPLE 12

Microgranules

From the composition obtained by the preceeding Example and having an active ingredient content of 5% microgranules are prepared according to the following method:

80% by weight of the powder mixture according to Example 11 are homogenized with 20% by weight of an 1% aqueous Berol E solution in a kneader. The soft material thus obtained is pressed through an extruder having the desired orifice. The filaments thus obtained are dried at 50° C. and ground to the desired size. The microgranules having the desired particle size are separated by sieving. The oversize particles are re-ground. The powder-form granules are added to the next batch. The microgranules thus obtained are suitable for use in agriculture by spreading on the soil.

One may also proceed by pressing pastilles from the homogenized mixture by means of an adhesive solution and drying the pastilles. Thus a sustained release plant growth regulating composition is obtained which may be placed into the soil.

EXAMPLE 13

Microgranules

10% by weight of the compound according to Example 3 are dissolved in 30% by weight of anhydrous ethanol. 200% by weight of diatomaceous granules (average particle size 2–3 mm) are fluidized in a batch-wise Glatt-type fluidization granulator whereupon the alcoholic solution of the active ingredient is sprayed onto the fluid layer. After removing the solvent microgranules having an active ingredient content of 5% by weight and suitable for soil-treatment are obtained.

We claim:

1. A compound of the Formula I

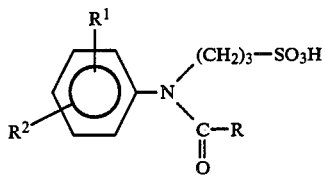

wherein $R^1$ and $R^2$ may be identical or different and stand for hydrogen, halogen, lower alkyl or lower alkoxy and R stands for furyl, halogen substituted lower alkyl, phenyl and halogen substituted phenyl and hydrates and salts thereof.

2. A compound according to claim 1 wherein $R^1$ and $R^2$ are lower alkyl and R is halogeno substituted lower alkyl.

3. N-2'-ethyl-phenyl-N-chloroacetyl-3-amino-propane-1-1-sulfonic acid and salts thereof.

4. N-2',6'-dimethyl-phenyl-N-chloroacetyl-3-amino-propane-1-sulfonic acid and salts thereof.

5. A salt of a compound of the formula I according to claim 1 formed with an alkali metal, alkaline earth metal or organic base.

6. A plant growth regulating composition comprising as active ingredient an effective amount of at least one compound of the Formula I as defined in claim 1, in admixture with a suitable inert solid or liquid carrier or diluent.

7. A plant growth regulating composition according to claim 6 comprising as active ingredient a compound of the Formula I wherein $R^1$ and $R^2$ are lower alkyl and R is halogeno substituted lower alkyl.

8. A plant growth regulating composition according to claim 7 wherein the active compound is N-2'-ethyl-phenyl-N-chloroacetyl-3-amino-propane-1-sulfonic acid or a salt thereof as active ingredient.

9. A plant growth regulating composition according to claim 7 wherein the active ingredient is N-2',6'-dimethylphenyl-N-chloroacetyl-3-amino-propane-1-sulfonic acid or a salt thereof.

10. A plant growth regulating composition according to claim 6 wherein an inert mineral substance or organic solvent is included as the carrier or diluent.

11. A plant growth regulating composition as defined in claim 6 in the form of a spray microgranulate, seed-dressing agent, seed-grain foil, spray wettable powder or emulsifiable concentrate.

12. A plant growth regulating composition according to claim 6 containing 0.001 to 95% by weight of active ingredient.

13. A method of regulating the growth of maize, sunflower, lettuce, cucumber, tomato, French beans and mustard plants which comprises: applying to the plants or to the seeds of the plants an effective amount of a composition as defined in claim 6.

14. A method of regulating the growth of maize, sunflower, lettuce, cucumber, tomato, French beans and mustard plants which comprises: applying to the plants or to the seeds of the plants an effective amount of a composition as defined in claim 7.

15. A method of regulating the growth of maize, sunflower, lettuce, cucumber, tomato, French beans and mustard plants which comprises: applying to the plants or to the seeds of the plants an effective amount of a composition as defined in claim 8.

16. A method of regulating the growth of maize, sunflower, lettuce, cucumber, tomato, French beans and mustard plants which comprises: applying to the plants or to the seeds of the plants an effective amount of a composition as defined in claim 9.

17. A method of regulating the growth of maize, sunflower, lettuce, cucumber, tomato, French beans and mustard plants which comprises: applying to the plants or to the seeds of the plants an effective amount of a composition as defined in claim 10.